(12) United States Patent
Barron

(10) Patent No.: US 6,581,640 B1
(45) Date of Patent: Jun. 24, 2003

(54) LAMINATED MANIFOLD FOR MICROVALVE

(75) Inventor: Richard J. Barron, Ann Arbor, MI (US)

(73) Assignee: Kelsey-Hayes Company, Livonia, MI (US)

( * ) Notice: Subject to any disclaimer, the term of this patent is extended or adjusted under 35 U.S.C. 154(b) by 0 days.

(21) Appl. No.: 09/640,132

(22) Filed: Aug. 16, 2000

(51) Int. Cl.[7] .............................. F15C 1/06; B44C 1/22; B31D 3/00
(52) U.S. Cl. ........................... 137/833; 216/41; 216/56; 216/66
(58) Field of Search .............................. 216/41, 56, 66; 137/833; 251/367

(56) References Cited

U.S. PATENT DOCUMENTS

| | | | |
|---|---|---|---|
| 3,467,124 A | * | 9/1969 | Simson ....................... 137/833 |
| 3,506,024 A | * | 4/1970 | Erwin et al. ................... 137/47 |
| 3,587,607 A | * | 6/1971 | Konig ......................... 137/833 |
| 3,680,576 A | * | 8/1972 | Kiwak ......................... 137/833 |
| 3,747,628 A | | 7/1973 | Holster et al. |

(List continued on next page.)

FOREIGN PATENT DOCUMENTS

| | | |
|---|---|---|
| DE | 4101575 | 7/1992 |
| DE | 4417251 | 11/1995 |

(List continued on next page.)

OTHER PUBLICATIONS

IEEE Technical Digest entitled "Compliant Electro–thermal Microactuators", J. Jonsmann, O. Sigmund, S. Bouwstra, Twelfth IEEE International Conference on Micro Electro Mechanical Systems held Jan. 17–21, 1999, Orlando, Florida, pp. 588–593, IEEE Catalog No.: 99CH36291C.

(List continued on next page.)

*Primary Examiner*—Kevin Shaver
*Assistant Examiner*—D A Bonderer
(74) *Attorney, Agent, or Firm*—MacMillan, Sobanski & Todd, LLC

(57) ABSTRACT

A manifold for distributing a fluid. The manifold can be used to distribute a fluid to and from a microvalve. The manifold includes a first plate having a groove formed in one face thereof. A second plate is fixed to the first plate so as to cover the groove to form a fluid passage through the groove. First and second bores are formed through at least one of the first plate and the second plate to form an inlet and an outlet, respectively, of the fluid passage. According to a method of manufacturing, etching the first plate forms the groove. Preferably, an etching process also forms the first and second bores. Also, preferably, the first plate is one of a plurality of plates formed from a single sheet of material. Preferably the sheet of material is a standard sized sheet with locating indicia enabling assembly of the manifold with standard pick and place equipment. Specifically, a method of assembling the manifold includes forming a plurality of first plates from a single sheet; a plurality of second plates from a second sheet; applying a braze material to selected portions of one of the first and second sheets; clamping the sheets together with each of the first plates aligned with a corresponding one of the second plates; heating the first and second sheets, and braze material therebetween, to braze each of the first plates to the corresponding one of the second plates to form a manifold; detaching each manifold from the first and second sheets; and assembling the manifold to a fluid circuit. Optionally, a microvalve is attached to each manifold before the manifold is detached from the first and second sheets.

4 Claims, 7 Drawing Sheets

U.S. PATENT DOCUMENTS

| | | | |
|---|---|---|---|
| 3,886,654 A | * | 6/1975 | Erdle ........................ 29/624 |
| 3,965,918 A | * | 6/1976 | Finkbeiner et al. ........... 137/83 |
| 4,110,140 A | * | 8/1978 | Laakaniemi et al. ........ 137/833 |
| 4,434,813 A | | 3/1984 | Mon |
| 4,581,624 A | | 4/1986 | O'Connor |
| 4,628,576 A | | 12/1986 | Giachino et al. |
| 4,647,013 A | | 3/1987 | Giachino et al. |
| 4,661,835 A | | 4/1987 | Gademann et al. |
| 4,821,997 A | | 4/1989 | Zdeblick |
| 4,824,073 A | | 4/1989 | Zdeblick |
| 4,826,131 A | | 5/1989 | Mikkor |
| 4,828,184 A | | 5/1989 | Gardner et al. |
| 4,869,282 A | | 9/1989 | Sittler et al. |
| 4,938,742 A | | 7/1990 | Smits |
| 4,943,032 A | | 7/1990 | Zdeblick |
| 4,959,581 A | | 9/1990 | Dantlgraber |
| 4,966,646 A | | 10/1990 | Zdeblick |
| 5,029,805 A | | 7/1991 | Albarda et al. |
| 5,050,838 A | | 9/1991 | Beatty et al. |
| 5,054,522 A | | 10/1991 | Kowanz et al. |
| 5,058,856 A | | 10/1991 | Gordon et al. |
| 5,061,914 A | | 10/1991 | Busch et al. |
| 5,064,165 A | | 11/1991 | Jerman |
| 5,065,978 A | | 11/1991 | Albarda et al. |
| 5,069,419 A | | 12/1991 | Jerman |
| 5,074,629 A | | 12/1991 | Zdeblick |
| 5,082,242 A | | 1/1992 | Bonne et al. |
| 5,096,643 A | | 3/1992 | Kowanz et al. |
| 5,131,729 A | | 7/1992 | Wetzel |
| 5,133,379 A | | 7/1992 | Jacobsen et al. |
| 5,142,781 A | | 9/1992 | Mettner et al. |
| 5,161,774 A | | 11/1992 | Engelsdorf et al. |
| 5,177,579 A | | 1/1993 | Jerman |
| 5,178,190 A | | 1/1993 | Mettner |
| 5,179,499 A | | 1/1993 | MacDonald et al. |
| 5,180,623 A | | 1/1993 | Ohnstein |
| 5,192,623 A | * | 3/1993 | Gewelber et al. ........... 428/593 |
| 5,197,517 A | | 3/1993 | Perera |
| 5,209,118 A | | 5/1993 | Jerman |
| 5,216,273 A | | 6/1993 | Doering et al. |
| 5,217,283 A | | 6/1993 | Watanabe |
| 5,238,223 A | | 8/1993 | Mettner et al. |
| 5,244,537 A | | 9/1993 | Ohnstein |
| 5,267,589 A | | 12/1993 | Watanabe |
| 5,271,431 A | | 12/1993 | Mettner et al. |
| 5,271,597 A | | 12/1993 | Jerman |
| 5,309,943 A | | 5/1994 | Stevenson et al. |
| 5,325,880 A | | 7/1994 | Johnson et al. |
| 5,333,831 A | | 8/1994 | Barth et al. |
| 5,355,712 A | | 10/1994 | Petersen et al. |
| 5,368,704 A | | 11/1994 | Madou et al. |
| 5,375,919 A | | 12/1994 | Furuhashi |
| 5,400,824 A | | 3/1995 | Gschwendtner et al. |
| 5,417,235 A | | 5/1995 | Wise et al. |
| 5,445,185 A | | 8/1995 | Watanabe et al. |
| 5,458,405 A | | 10/1995 | Watanabe |
| 5,566,703 A | | 10/1996 | Watanabe et al. |
| 5,683,828 A | * | 11/1997 | Spear et al. ................... 429/13 |
| 5,785,295 A | | 7/1998 | Tsai |
| 5,812,378 A | * | 9/1998 | Fjelstad et al. ............. 361/767 |
| 5,854,507 A | * | 12/1998 | Miremadi et al. .......... 257/685 |
| 5,863,671 A | * | 1/1999 | Spear, Jr. et al. ............ 429/12 |
| 5,909,078 A | | 6/1999 | Wood et al. |
| 5,941,608 A | | 8/1999 | Campau et al. |
| 5,954,079 A | | 9/1999 | Barth et al. |
| 5,955,817 A | | 9/1999 | Dhuler et al. |
| 5,970,998 A | | 10/1999 | Talbot et al. |
| 5,976,910 A | * | 11/1999 | Tamura et al. .............. 438/107 |
| 5,985,164 A | * | 11/1999 | Chu et al. ..................... 216/41 |
| 5,994,816 A | | 11/1999 | Dhuler et al. |
| 6,019,437 A | | 2/2000 | Barron et al. |
| 6,023,103 A | * | 2/2000 | Chang et al. ............... 257/781 |
| 6,023,121 A | | 2/2000 | Dhuler et al. |
| 6,038,928 A | | 3/2000 | Maluf et al. |
| 6,090,301 A | * | 7/2000 | Mizukoshi et al. ........... 216/17 |
| 6,114,794 A | | 9/2000 | Dhuler et al. |
| 6,177,203 B1 | * | 1/2001 | Garcia ........................ 165/166 |
| 6,248,151 B1 | * | 6/2001 | Horine ........................ 75/335 |
| 6,321,791 B1 | * | 11/2001 | Chow ........................ 137/827 |

FOREIGN PATENT DOCUMENTS

| | | |
|---|---|---|
| DE | 4422942 | 1/1996 |
| EP | 0250948 | 1/1988 |
| EP | 0261972 | 3/1988 |
| WO | WO 99/16096 | 4/1999 |
| WO | WO 00/14415 | 3/2000 |

OTHER PUBLICATIONS

"A Silicon Microvalve For The Proportional Control Of Fluids" by K.R. Williams, N.I. Maluf, E.N. Fuller, R.J. Barron, D.P. Jaeggi, and B.P. van Drieënhuizen, Transducers '99, Proc. $10^{th}$ International Conference on Solid State Sensors and Actuators, held Jun. 7–10, 1999, Sendai, Japan, pp. 18–21.

Internet web page http://www.electronicmaterials.com/businesses/sem/amorph/page5_1_1_2.htm, copyright 2000 by Honeywell, printed Aug. 24, 2000.

Internet web page http://www.hitecmetalgroup.com/eng-prod.htm, by HI TecMetal Group, Inc., printed Aug. 24, 2000.

Advertisement, "HI TecMetal Group Develops Niche Market for Brazed Laminated Assemblies", Fluid Power Journal, Sep./Oct. 1999 issue, p. 27.

Noworolski et al., "Process for in–plane and out–of–plane single–crystal–silicon thermal microactuators," Sensors and Actuators A, Elsevier Science S.A., vol. 55, No. 1, (1996) 65–69.

Ayón et al., "Etching Characteristics and Profile Control in a Time Multiplexed ICP Etcher," Proc. of Solid State Sensor and Actuator Workshop Technical Digest, Hilton Head SC, (Jun. 1998) 41–44.

Bartha et al., "Low Temperature Etching of Si in High Density Plasma Using $SF_6/O_2$," Microelectronic Engineering, Elsevier Science B.V., vol. 27, (1995) 453–456.

Fung et al., "Deep Etching of Silicon Using Plasma" Proc. of the Workshop on Micromachining and Micropackaging of Transducers, (Nov. 7–8, 1984) 159–164.

Klaassen et al., "Silicon Fusion Bonding and Deep Reactive Ion Etching; A New Technology for Microstructures," Proc., Transducers 95 Stockholm Sweden, (1995) 556–559.

Linder et al.,"Deep Dry Etching Techniques as a New IC Compatible Tool for Silicon Micromachining," Proc,. Transducers, vol. 91, (Jun. 1991) 524–527.

Petersen et al., "Surfaced Micromachined Structures Fabricated with Silicon Fusion Bonding," Proc. Transducers, vol. 91, (Jun. 92) 397–399.

Yunkin et la., "Highly Anisotropic Selective Reactive Ion Etching of Deep Trenches in Silicon," Microelectronic Enginineering, Elsevier Science B.V., vol. 23, (1994) 373–376.

* cited by examiner

LAMINATED MANIFOLD FOR MICROVALVE

BACKGROUND OF THE INVENTION

This invention relates in general to MicroElectroMechanical Systems, and in particular, to a manifold for distributing a fluid to and from a microvalve.

MicroElectroMechanical Systems (MEMS) is a class of systems that are physically small, having features with sizes in the micrometer range. These systems have both electrical and mechanical components. The term "micromachining" is commonly understood to mean the production of three-dimensional structures and moving parts of MEMS devices. MEMS originally used modified integrated circuit (computer chip) fabrication techniques (such as chemical etching) and materials (such as silicon semiconductor material) to micromachine these very small mechanical devices. Today there are many more micromachining techniques and materials available. The term "microvalve device" as used in this application means a complete, functioning valve having features with sizes in the micrometer range, and thus is by definition at least partially formed by micromachining. Furthermore, a "microvalve device", as used in this application includes a microvalve, and may include other components such as a fluid distributing manifold, pressure, temperature, flow or other types of sensors, pumps or other valves of various types. It should be noted that if components other than a microvalve are included in the microvalve device, these other components may be micromachined components or standard sized (larger) components.

Various microvalve devices have been proposed for controlling fluid flow within a fluid circuit. A typical microvalve device includes a displaceable member or valve movably supported by a body. Depending on the type of valve, the valve may be operatively coupled to an actuator for movement between a closed position and a fully open position. When placed in the closed position, the valve blocks or closes a first fluid port that is placed in fluid communication with a second fluid port, thereby preventing fluid from flowing between the fluid ports. When the valve moves from the closed position to the fully open position, fluid is increasingly allowed to flow between the fluid ports.

A manifold can be used to provide an interconnection between the physically minute and normally closely spaced ports of a microvalve and associated macro sized fluid conduits of the system in which the microvalve is installed.

On a macro scale, it is known to individually laminated assemblies, such as valve manifolds, from uniquely styled stamped laminations. Stamped laminations are stacked to the desired thickness and are held together by a variety of welding methods or with pins or bushings. During the set-up process copper rings or slugs are added at pre-determined locations. In a brazing process, the copper liquefies and flows into all joints forming a strong iron-copper alloy bond that is the heart of the process. All the components are bonded into a single unit having strength often greater than one-piece construction. Such a process is performed by HI TecMetal Group of Cleveland, Ohio.

Also on a macro scale, U.S. Pat. No. 3,747,628 to Holster et al. describes making a fluidic function module for use in a system for constructing fluidic logical and/or analog circuits. The module includes a basic part that comprises three plates and a hood that may be made, for example, of a suitable synthetic material by injection molding. Clamped between them are three diaphragms that provide airtight seals. The plate is provided with an annular valve seat that cooperates with a disc-shaped valve made of a resilient material. In its lower position shown in the drawing the valve cooperates with the annular valve seat, but in its upper position it is capable of cooperating with a valve seat in the plate. The diaphragm through an annular part of smaller thickness is integral with a movable part that has a specially shaped cross-section, the part being referred to as the movable part of the circuit element. A fluidic function module consists of a basic part, a gasket, and a connecting part in the form of a "universal connecting plate". The universal connecting plate is made of a synthetic material, for example by injection molding, so that the product may simply be manufactured by mass production methods. The universal function connecting plate is provided in both of it's surfaces with grooves and bores which together form a standard passage system. When the basic part is assembled with the gasket and the universal connecting plate, the combination forms a fluidic module for constructing fluidic circuits which, depending upon the intended use, comprise one or more fluidic modules for performing logical analog and/or combined operations, the function module comprising at least firstly a basic part accommodating a plurality of individual fluidic circuit elements and secondly a function connecting part in the form of the universal connecting plate in which passages have been formed which interconnect the various input, output, air supply and vent passages of the individual circuit elements of the basic part in the appropriate manner, so that the assembly of basic part and connecting part forms a function module which may have, for example, an AND, an OR, a universal or a storage function. Adapting the universal function connecting plate to an intended function of a function module is achieved by removing readily removable partitions of the function connecting plate from between specific passages of the standard passage system on opposite sides of the universal function connecting plate. The partitions are removed by drilling between the passages.

SUMMARY OF THE INVENTION

The invention relates to a manifold for distributing a fluid. The manifold can be used to distribute a fluid to and from a microvalve. The manifold includes a first plate having a groove formed in one face thereof. A second plate is fixed to the first plate so as to cover the groove to form a fluid passage through the groove. First and second bores are formed through at least one of the first plate and the second plate to form an inlet and an outlet, respectively, of the fluid passage. Preferably, the face of the first plate or the second plate opposite the face with the grooves formed therein has a solderable pad formed on at least a portion thereof. According to a method of manufacturing, etching the first plate forms the groove. Preferably, an etching process also forms the first and second bores. Also, preferably, the first plate is one of a plurality of plates formed from a single sheet of material. Preferably the sheet of material is a standard sized sheet with locating indicia enabling assembly of the manifold with standard pick and place equipment. Specifically, a method of assembling the manifold includes forming a plurality of first plates from a single sheet; a plurality of second plates from a second sheet; applying a braze material to selected portions of one of the first and second sheets; clamping the sheets together with each of the first plates aligned with a corresponding one of the second plates; heating the first and second sheets, and braze material therebetween, to braze each of the first plates to the corresponding one of the second plates to form a manifold;

detaching each manifold from the first and second sheets; and assembling the manifold to a fluid circuit. Optionally, a microvalve is attached to each manifold before the manifold is detached from the first and second sheets.

Various other objects and advantages of this invention will become apparent to those skilled in the art from the following detailed description of the preferred embodiments, when read in light of the accompanying drawings.

DETAILED DESCRIPTION OF THE PREFERRED EMBODIMENT

Figure 1:
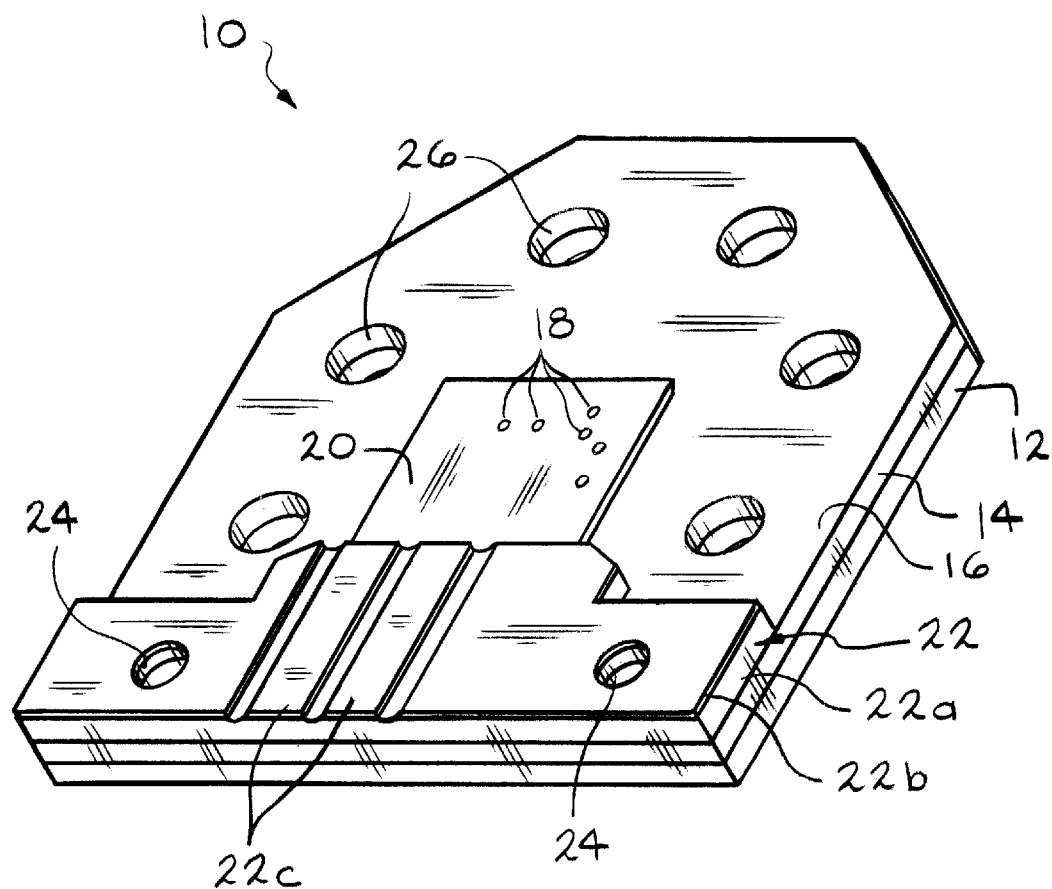
FIG. 1 is a perspective view of a two-layer manifold according to the invention.

Referring now to the drawings, there is illustrated in FIG. 1 a first embodiment of a laminated manifold 10 according to the present invention. The manifold includes a first plate 12 and a second plate 14 fixed to the first plate 12. Each of the first plate 12 and the second plate 14 is preferably formed from a flat metallic sheet material and fixed to one another according to any suitable method. As will be discussed below, a preferred method of fixing the first plate 12 to the second plate 14 is by brazing the two plates together. Any suitable material may be used to form the first plate 12 and second plate 14; one suitable material is believed to be a low expansion 42% nickel-steel alloy. As shown, the second plate 14 has an outer surface 16 through which a plurality of openings 18 are formed. The openings 18 enable fluid communication between passages (to be discussed below) in the manifold 10 and a component external to the manifold, such as a microvalve 19 (shown in FIG. 6) fixed to the outer surface of the second plate 14. Various microvalves and methods of attaching the microvalves to a substrate, such as the instant manifold 10, are discussed in co-pending U.S. patent application Ser. No. 09/533,893, filed Mar. 22, 2000, and Ser. No. 09/605,591, filed Jun. 27, 2000, the disclosures of which are incorporated herein by reference. A bond pad 20 is preferably formed on a selected portion of the outer surface 16, about the openings 18. The bond pad 20 is suitably formed of a metallic material according to a method to be described below. A terminal block 22 is fixed to the outer surface 16 near the bond pad 20. The terminal block 22 is fixed to the manifold 10 by any suitable means, such as a mechanical fastener, such as a rivet or a bolt, by a suitable adhesive, or by soldering the terminal block 22 to a second bond pad (not shown) formed on the outer surface 16. The terminal block 22 may suitably be constructed similar to a printed circuit board, including a non-conductive substrate 22a, and at least one copper or copper alloy layer 22b bonded to the substrate 22a. A second copper or copper alloy layer (not shown) may be fixed to the surface of the substrate 22a, which would allow the attachment of the terminal block 22 to the second bond pad by soldering. The layer 22b is cut or etched through at various locations to form electrically separate terminal solder pads 22c. Electrical connections between conductors (not shown) from an external electrical circuit and from conductors (not shown) from the microvalve 19 or other components mounted on the manifold can be completed by soldering associated ones of the conductors to individual solder pads 22c. In the illustrated embodiment, two terminal mounting bores 24 are formed through the terminal block 22 and through the manifold 10. An additional six manifold mounting bores 26 are formed through the manifold 10. Threaded fasteners (not shown) are inserted through the bores 24 and 26 and engage a mounting substrate (not shown) to fasten the terminal block 22 to the manifold 10 and to fasten the manifold 10 to the mounting substrate. The mounting substrate may be any suitable surface, such as a pump motor block in an electronically controlled braking system (not shown) or a suitable circuit board having electronic circuits and/or fluidic circuits and connections thereon.

Figure 2:
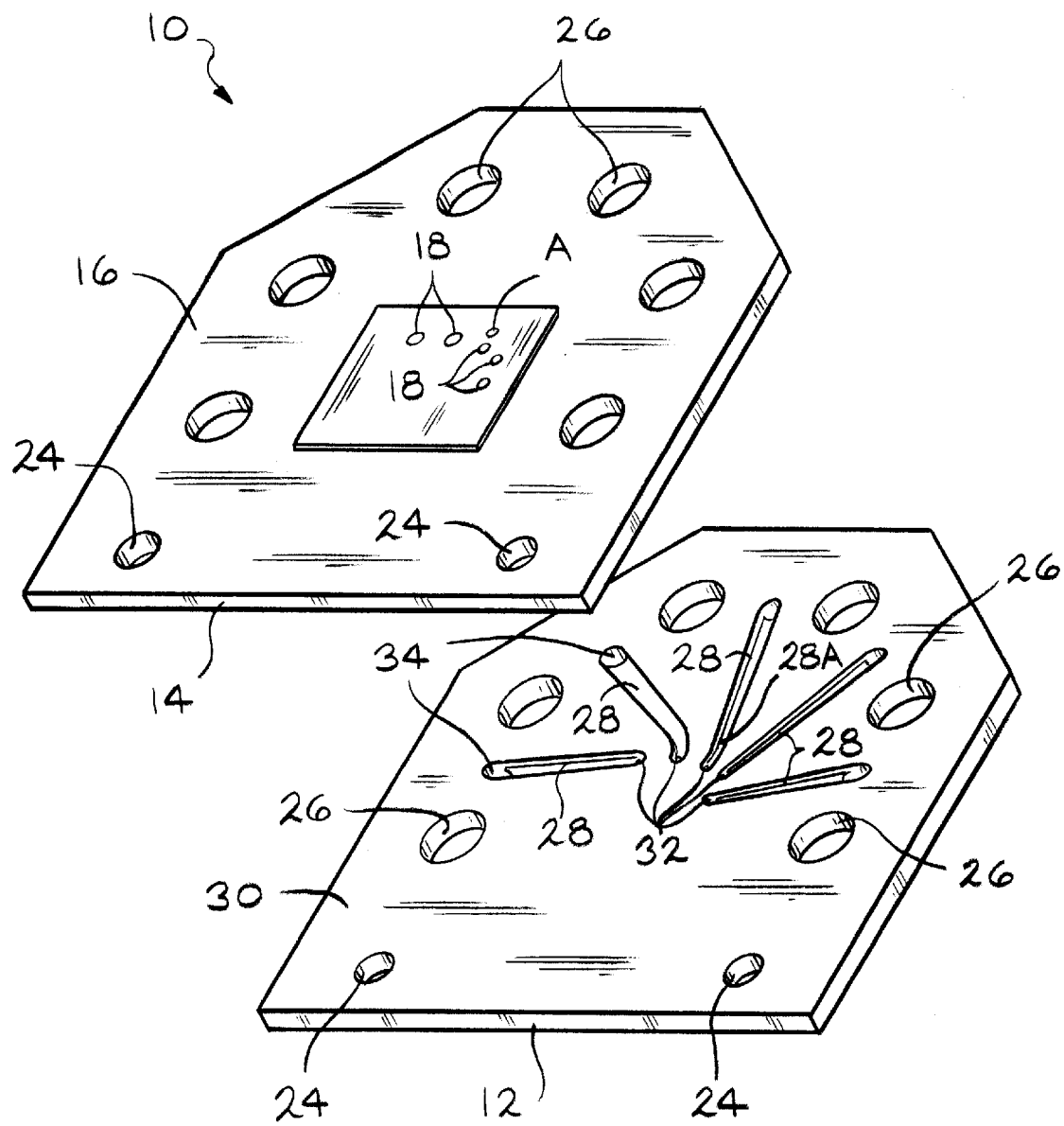
FIG. 2 is an exploded view of the manifold shown in FIG. 1.
Figure 3:
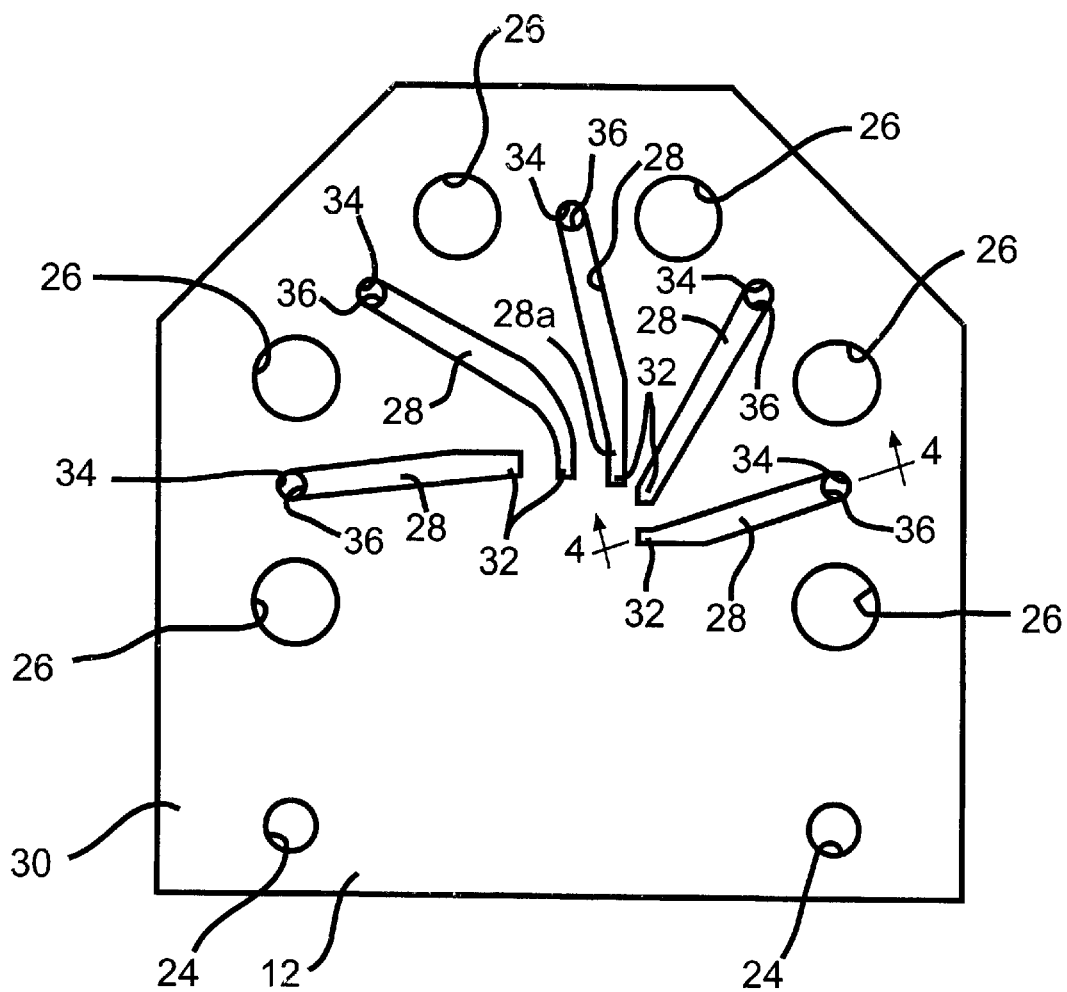
FIG. 3 is a plan view of a first plate forming the manifold of FIGS. 1 and 2

Referring now to FIG. 2, the manifold 10 is shown in an exploded view. It will be appreciated that the bores 24 and 26 extend through both the first plate 12 and the second plate 14. Additionally seen in FIG. 2, and seen in plan view in FIG. 3, are a plurality of grooves 28 formed in an inner surface 30 of the first plate 12. The grooves 28 are seen to fan outwardly from a central region where the grooves 28 are in communication with the openings 18 in the second plate 14. Each groove 28 has an inner end 32 adjacent a respective one of the openings 18, except one of the grooves 28 which communicates, at a location 28A, with an additional opening 18 indicated at "A", the purpose of which will be explained below. Each groove 28 also has an outer end 34. At the outer end 34 each groove 28 communicates with a respective bore 36 through the first plate 12.

Figure 4:
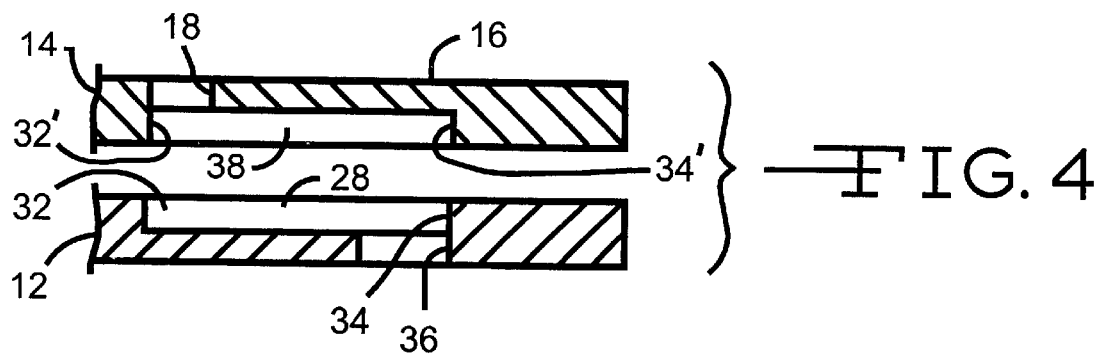
FIG. 4 is an exploded view taken along line 4—4 of FIG. 3.

FIG. 4 shows an exploded view of a section taken through the manifold 10 along the line 4—4, which line extends along one of the grooves 28. Like the first plate 12, the second plate 14 is provided with a plurality of grooves 38 (one of which is shown in FIG. 4). The grooves 38 fan outwardly from associated ones of the openings 18. Each of the grooves 38 is aligned with and co-extensive with an associated one of the grooves 28 in the first plate 12, extending from an inner end 32' opposite the inner end 32 of the associated groove 28 in the first plate 12 to an outer end 34' opposite the outer end 34 of the associated groove 28 in the first plate 12.

Referring now also to FIG. 12, the manifold 10 may be manufactured according to any suitable method. One method, according to the invention, includes as a first step 101 forming the first plate 12. The plate 12, as indicated above, may be formed of any suitable sheet material, such as sheet steel. The first plate 12 is preferably formed by isotropic photo-etching process techniques, with features being simultaneously etched from both sides of the sheet material. For example, the grooves 28 are etched into the inner surface of the plate 12. Simultaneously, pits are etched into the outer surface of the plate 12, where the bores 36 are to be formed. The grooves 28 and the pits are each etched halfway through the material of the plate 12. Where these pits coincide meet the grooves 28, the bores 36 through the plate 12 are formed. It is also contemplated that the first plate 12 (and the second plate 14) may be formed by any other suitable process, including stamping, or machining using processes such as cutting (for example, by laser), drilling, milling, etc.

Figure 5:
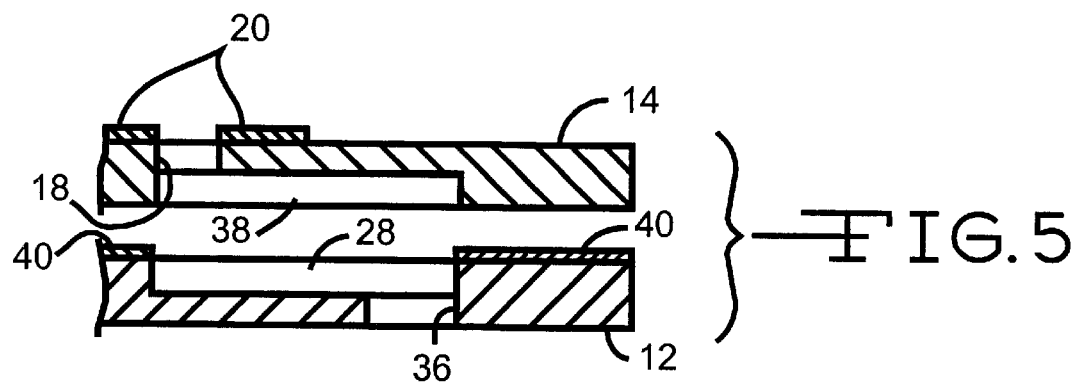
FIG. 5 is a view similar to FIG. 4, except showing a second plate with a selectively applied copper coating.
Figure 11:
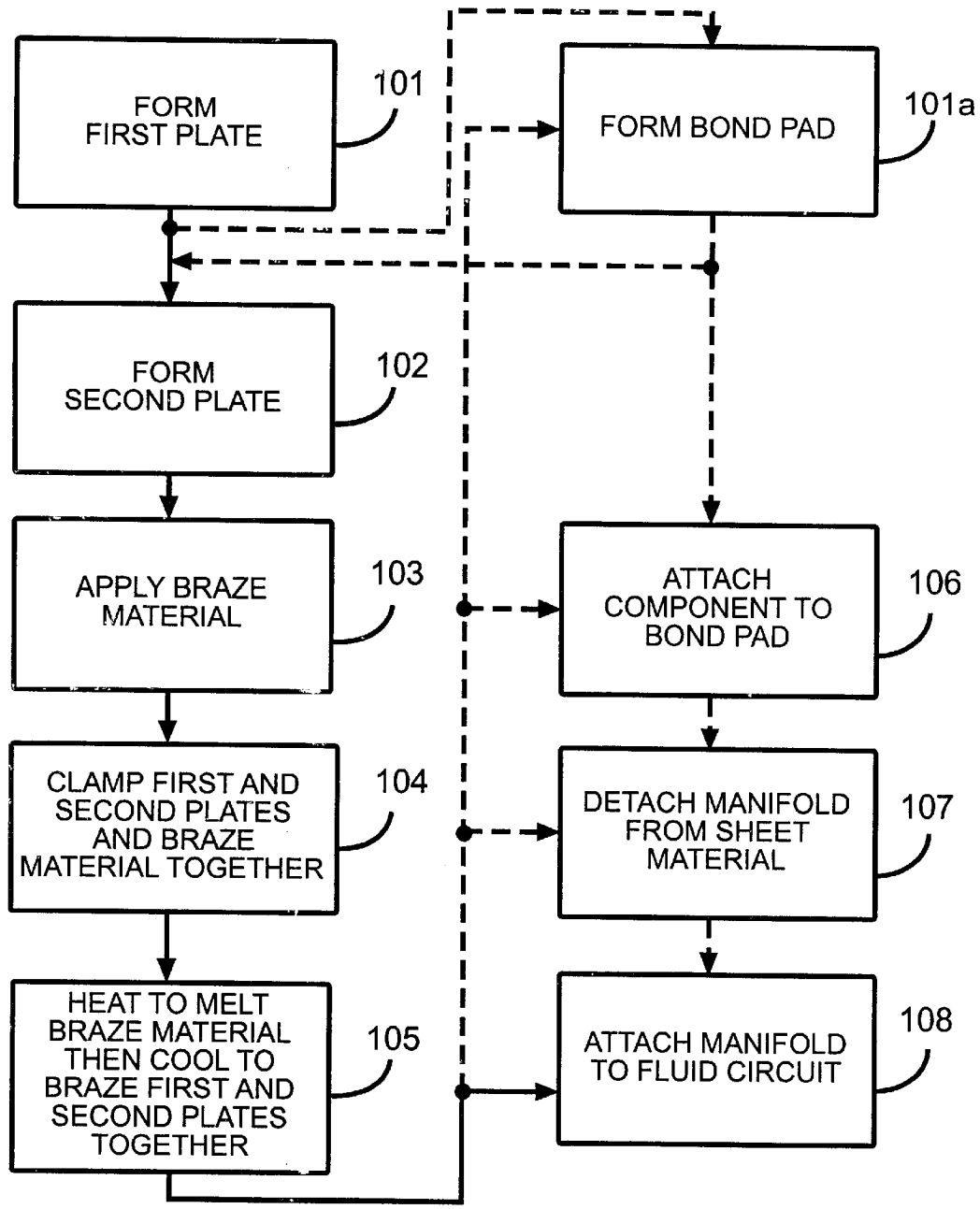
FIG. 11 is a flow diagram illustrating a method of manufacturing the manifold.

In a step 101a, the bond pad 20 may be formed on a sheet material from which the second plate 14 will be formed, prior to etching/stamping, or otherwise forming the second plate 14. The bond pad 20 may be formed by any suitable process, including, preferably, a photo-printing process, or any other suitable process, including screen printing, plating, vapor deposition, or other forms of metal deposition, of any material suitable for soldering. Preferably, the outer surface 16 of the second plate is selectively plated with copper to form the bond pad 20. Preferably, as shown in FIGS. 5 and 11, the bond pad 20 may be formed on the second plate 14 subsequent to forming the second plate 14 as described below. The bond pad 20 may also be formed even later in the manufacturing process, simultaneously with, or after the first plate 12 and the second plate 14 being fixed together. In another preferred embodiment, the bond pad 20 is formed of pure nickel. The bond pad 20 will require a masking and plating operation, using photo-resist laminated to the part to mask off the non-plated areas of the second plate 14. Preferably one will avoid plating the second plate 14 inside the openings 18 (if plating occurs after the forming of the second plate 14) as solder could then flow into these areas, obstructing the openings 18. This could be avoided by plating the bond pad 20 prior to etching the openings 18 into the second plate 14. This may not be possible if the etch rate of the bond pad 20 is much greater than the underlying metal (e.g. a copper pad on steel sheet material). Selectively masking the openings 18 would increase the area of the first and second plates 12, 14 which will be subject to the pressure of the fluids subsequently introduced into the openings 18 (into the non-brazed gap between the first plate 12 and the second plate 14 in the previously masked off areas around the openings 18) whilst reducing the size of the soldered area fixing the component (e.g., the microvalve 19) to the second plate 14. This may be a problem on closely spaced ports, as the solder material surrounding the openings 18 form part of the pressure boundary of a fluid conduit between the component (e.g., the microvalve 19) and the second plate 14 to channel fluid between a particular opening 18 and the associated port in the component (e.g., the microvalve 19). If there is no solder between adjacent ones of the openings 18, then the fluid from one of the openings would be able to flow to a port associated with a different opening 18.

In a step 102, the second plate 14 is formed. The plate 14 may be formed of any suitable material. In a preferred embodiment, to enable a good match between the expansion characteristics of a microvalve formed of a silicon material to be attached to the bond pad 20, the second plate 14 is formed from a sheet material that has a relatively low expansion characteristic. More preferably, the first plate 12 is also formed of the sheet material with low expansion characteristics. For example, the sheet material may be low expansion 42% Ni steel alloy. Alternatively, the second plate 14 could be formed of any suitable sheet material and fixed (by any suitable process, including welding, brazing (in conjunction with a separate step to be described below for brazing the first plate 12 to the second plate 14), various forms of metal deposition, etc.) to a small extra piece of low expansion sheet material (just in the region where the bond pad 20 is to be formed). The second plate 14 is preferably formed by photo-etching in a manner similar to the first plate 12, but, as with the first plate 12, may be formed by any suitable process.

As indicated above, subsequent to forming the second plate 14 in the step 102, the bond pad 20 may formed in a step 101a.

In a step 103, a braze material 40 is placed between the first plate 12 and the second plate 14. If the bond pad 20 is already formed on the first plate 12, the braze material 20 will be a braze alloy with a lower melting point than the bond pad 20. For example, if the bond pad is formed of pure nickel, which has a melting point of 1453 degrees Centigrade, the braze material 40 could suitably be copper with a melting point of 1083. The brazing temperature in a subsequent brazing step to be discussed below could then be, for example, 1150 to 1250 degrees Centigrade. If, on the other hand, the bond pad is formed of copper, the braze material could be, for example, electroless nickel (11%–12% Platinum) with a melting point of 880 degrees Centigrade, resulting in a preferred brazing temperature range of 930 to 1030 degrees Centigrade. Preferably, the braze material 40 is selectively plated over the inner surface of the second plate, as shown in FIG. 5. However, various other methods of introducing the braze material 40 between the first plate 12 and the second plate 14 are contemplated. For example, the braze material 40 may be selectively plated to the inner surface of the second plate 14. Another method of introducing the braze material 40 is to introduce the braze material 40 in the form of an appropriately patterned foil inserted between the first plate 12 and the second plate 14. Examples of foils which may be suitable include MET-GLAS® Brazing Foils (MBF) from Honeywell Electronic Materials (Sunnyvale, Calif.); this material is currently described on the Internet at http://www.electronicmaterials.com/businesses/sem/amorph/page5_1_1_2.htm.

Figure 6:
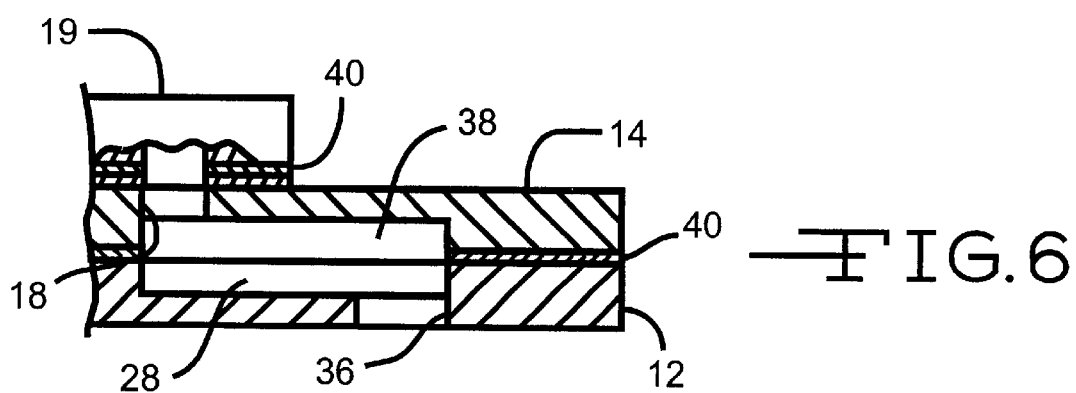
FIG. 6 is a view similar to FIG. 4, except showing the first plate and a second plate brazed together to form the manifold of FIG. 1.

In a step 104, the first plate 12 and the second plate 14 are aligned and the inner surfaces thereof are fixed to one another, as shown in FIG. 6. In the preferred embodiment, the first plate 12 and the second plate 14 are clamped to one another with the braze material 40 disposed therebetween, with all three properly aligned to cause the braze material to contact the first plate 12 and the second plate 14 at desired locations.

According to a step 105, the clamped-together assembly is then heated by any suitable method, such as, but not limited to, heating the assembly in a braze oven. The clamped-together assembly is heated to an appropriate brazing temperature range (as discussed above) for a sufficient length of time for the braze material 40 to melt.

In a second part of the step 105, the clamped-together assembly is cooled to allow the braze material 40 to solidify. The first plate 12 and the second plate 14 will be brazed together, forming the high integrity laminated manifold 10 with passageways 42 to connect from wide spaced larger bores 36 to the relatively smaller and more closely spaced openings 18 in the area of the bond pad 20. Each of the grooves 28 in the first plate 12 cooperates with a corresponding one of the grooves 38 in the second plate 14 (together with the adjoining portion of the braze material 40 along the grooves 28 and 28) to form each of the passageways 42.

It should be understood that the manifold 10 may be manufactured in any suitable fashion. It is contemplated, for example, that instead of providing the braze material 40 and brazing the first plate 12 and the second plate 14 together as described in the steps 104 and 105, the first plate 12 and the second plate 14 may be joined together by welding, or by mechanical fastenings, such as bolts or rivets. If leakage between the passageways 42 resulting from such a fastening method is not acceptable, it is contemplated that this may be addressed in conventional ways. For example, a gasket with suitable openings formed therethrough (corresponding to the passageways 42) may be provided between the first plate 12 and the second plate 14.

As noted above, in the embodiment illustrated in FIG. 2, one of the grooves 28 communicates, at the associated end 32 and at the location 28A, with two of the openings 18. Having multiple ones of the openings 18 in fluid communication with one another through a single groove 18 (passageway 42) is useful to distribute the pressure in the groove 18 to multiple parts of the component fixed to the bond pad 20 (for example, to provide pressure balancing in the microvalve 19).

Figure 7:
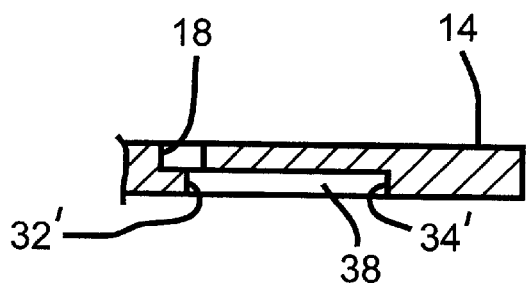
FIG. 7 is a view similar to FIG. 5, except showing a first step in forming angled ports in the manifold.
Figure 8:
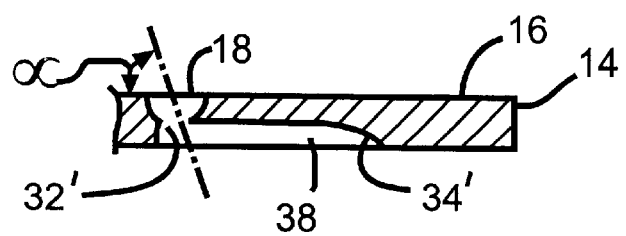
FIG. 8 is a view similar to FIG. 7, except showing a second step in forming angled ports in the manifold.

Referring now to FIG. 7, there is shown a view of an alternate embodiment of the second plate 14. The view in FIG. 7 is similar to the view in FIG. 4, except that the center of the opening 18 in the outer surface 16 of the second plate 14 is offset from the inner end 32' of the groove 38. The views in FIGS. 4 through 7 are idealized views of the laminations (the first plate 12 and the second plate 14) of the manifold 10, and do not show the rounded corners that actually result from an etching process. The isotropic photoetching process that is preferably used to form the first plate 12 and the second plate 14 actually gives rounded corners. When two holes are offset in opposite sides of a lamination as shown in FIG. 7, a sloping bore will normally actually result, as shown in FIG. 8, wherein a bore 18' is shown formed at an acute angle α to the outer surface 16. This non-perpendicular angled bore 18' is a design feature that can be used to help reduce the flow restriction or control fluid entry/exit angles in the complete manifold 10. This may be useful, for example, to balance flow forces acting on moving parts of a microvalve attached to the bond pad 20 of the manifold 10. Of course, if the laminations of the manifold 10 are formed by machining processes, such as drilling or cutting, angled ports may be formed by such machining processes, or other suitable process.

Figure 9:
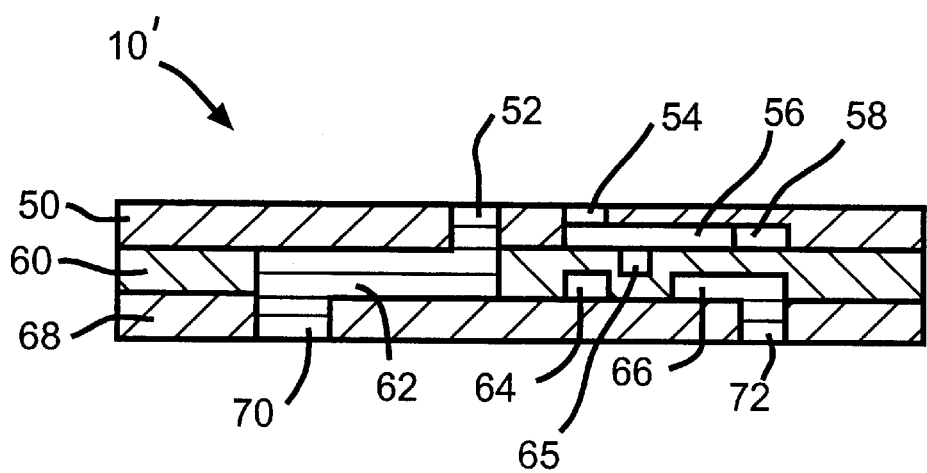
FIG. 9 is a view similar to FIG. 6, except showing a 3-layer manifold.

Referring now to FIG. 9, there is shown another alternate embodiment of the manifold, indicated at 10'. Instead of two laminations made of the first plate 12 and the second plate 14 like the manifold 10, the manifold 10' has three laminations, including a first plate 68, a second plate 50, and a third plate 60 disposed between the first plate 68 and the second plate 50. The manifold 10' is shown with some exemplary features (the purposes of which will not be described) that can be formed in a manner similar to the features described above with respect to the manifold 10, i.e., preferably formed using an isotropic photo-etching process to form the individual laminations, followed by a brazing process to join the laminations together. For example, the second plate 50 has a bore 52 formed therethrough by etching a circular area on each of an inner and an outer surface thereof, such that when the pits formed by the etching process meet, a through-bore is formed. An opening 54 is formed by etching the outer surface of the second plate 50 which communicates with a groove 56 formed by etching the inner surface of the second plate 50; where the pit formed by etching the opening 54 meets the groove 56, a through-bore is formed. The groove 56, at an end opposite to the through-bore to the opening 54, communicates with a transversely extending groove 58. Each of the grooves 56 and 58 cooperate with a flat surface of the third plate 60 to form a passageway. It will be appreciated that the passageways formed by the grooves 56 and 58 have half the cross-sectional area of the passageways formed by the two cooperating grooves in the first plate 12 and the second plate 14, which may be perfectly adequate for certain applications. The third plate 60 has an elongate opening 62 formed therethrough. The opening 62 may be formed, for example, by etching grooves in opposed locations on each face of the third plate 60; where the grooves meet, an elongate throughbore is formed. The third plate 60 is also shown to have a pair of grooves 64 and 66 formed in a lower face thereof (as viewed in FIG. 9), and a groove 65 formed in an upper face thereof. The groove 65 extends at right angles to the groove 56 formed in the second plate 50, and where the groove 56 overlaps the groove 65, the respective passageways formed by the grooves 56 and 65 are in fluid communication. The first plate 68 has two bores 70 and 72 formed therethrough in a manner similar to the bore 52 in the second plate 50.

Thus it is seen from the manifold 10' that the same techniques used to form the manifold 10 may be used for forming manifolds with multiple layers (indeed, as will be appreciated, manifolds of four or more laminations, although not shown, may be formed using the same techniques). Note that laminations similar to the third plate 60 which are to be brazed on both sides may not need selective plating techniques provided that a surface layer of braze material within the passageways is acceptable. The use of three or more laminations allows more complex (compared to the two layer manifold 10) porting and interconnection of passages such as may be required for particular (e.g., the microvalve 19), or components, to be attached to and in fluid communication with the manifold 10' thus formed. Note also that both large (equivalent in thickness to one lamination) and small (equivalent thickness to half of one lamination) passageways may be created. Indeed very large passageways can be formed by forming a halfthickness groove in one lamination that is aligned with and co-extensive with an associated elongated opening similar to the elongated opening 62 in one or more layers of the multiple lamination manifold, thereby forming a passageway which is equivalent in thickness to one and a half times (or two and a half times, etc.) the thickness of one lamination. Of course, a second half-thickness groove could be formed in a lamination on the opposite side of the intermediate lamination (or laminations) with the elongated opening therethrough, so as to form a passageway with is equivalent to two times (or three times, etc.) the thickness of a single lamination of the manifold.

Referring again to FIG. 11, following the joining of the first plate 12 and the second plate 14 to form the manifold 10, if not previously accomplished as described above, the bond pad 20 may now be formed on the outer surface 16 of the second plate 14. This may be accomplished by any suitable method in the step 101a, such as selectively plating copper material onto select portions of the outer surface 16. Additionally, as discussed above, if the terminal block 22 is to be attached to the manifold 10 by soldering, an suitable terminal block bond pad (not shown) is additionally formed on the outer surface 16 at the point where the terminal block 22 is to be attached.

A step 106 and a step 107 shown in FIG. 11 are optional, and will be described below.

In a step 108, the manifold 10 is attached to a fluid circuit (not shown). The manifold 10 may be, for instance, attached to a valve block of an Electro-Hydraulic Brake system (not shown). The valve block could be, for instance, formed with a flat surface to which the manifold 10 is to be mated. Fluid passages in the valve block would terminate in openings through the flat surface of the valve block, which are arranged to be spaced in mirror image to the bores 36 in the outer surface of the first plate 12. An annular groove could be machined about each of the openings in the flat surface, into which o-rings are inserted so as to be compressed between the bottom of the annular groove and the manifold 10 when the manifold 10 is fixed to the valve block. Of course, any suitable method may be used to prevent leakage of fluid at this interface between the bores 36 and the passages in the valve block; for example, a gasket with suitably formed openings could be substituted for the annular grooves and o-rings in certain applications. Threaded recesses (not shown) formed in the flat surface in mirror image to the terminal block mounting bores 24 and the manifold mounting bores 26 formed in the outer surface of the first plate 12 could be provided to receive threaded fasteners extending through the bores 24, 26 to fix the manifold 10 to the flat surface of the valve block and the terminal block 22 to the manifold 10. In a preferred embodiment of the invention, automated pick and place equipment (of the type used in manufacturing integrated circuits) is used to place the manifold 10 onto the flat surface to which the manifold 10 is being attached. Preferably, automated machinery fastens the manifold 10 to the flat surface (for example, by using threaded fasteners, or any other suitable method such as fastening the manifold 10 to the flat surface by clamps, welding, staking or forming the edges of a recess in the manifold 10 is mounted, mounting of additional components which act to hold the manifold 10 in place, etc.).

Preferably, in the step 106 prior to the step 108, the component to be attached to the manifold 10 (e.g., the microvalve 19) is attached using any suitable method and components. If the component (e.g., the microvalve 19) is to be soldered to the bond pad 20, solder is applied to the bond pad 20. This may be done in any suitable fashion. For example, solder paste may be screen-printed onto the bond pad 20 area. Another method contemplated for applying solder to the bond pad 20 is to selectively plate the solder on to the bond pad area. A solder pre-form may be used to distribute solder at the desired location of the bond pad 20. The component (e.g., the microvalve 19) is then soldered to the manifold 10. For example, the microvalve 19 may be formed from a silicon chip, and may have a suitable solderable metal deposited thereon, such as copper. The microvalve 19 thus may be provided with a copper (or other suitable material) bond area that may be soldered to the bond pad 20 to fix the microvalve 19 to the manifold 10. Additionally, if the terminal block 22 is to be soldered to the manifold 10, the terminal block 22 may be soldered to the terminal block bond pad. Of course, as described above, any suitable arrangement may be used to attach the terminal block 22 to the manifold 10, if a terminal block 22 is to be used at all. In a preferred embodiment of the invention, automated equipment of the type used in manufacturing integrated circuits is used to place the component (e.g., the microvalve 19) onto the bond pad 20, and the terminal block 22 onto the terminal block bond pad, and to solder the component to the bond pad 20, and the terminal block 22 to the terminal block bond pad.

Figure 10:
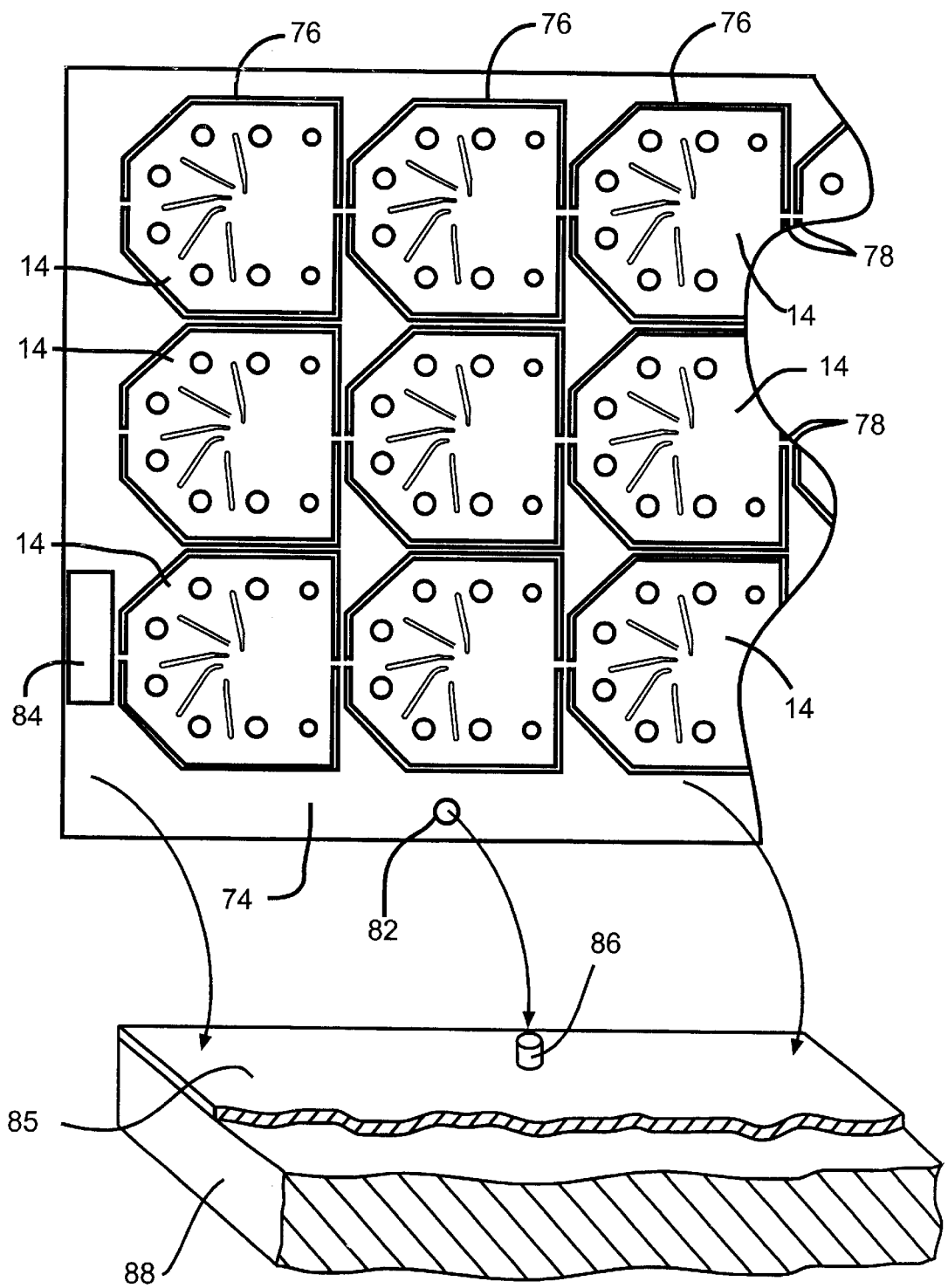
FIG. 10 is a plan view of a sheet from which is formed a plurality of first plates.

Referring now to FIG. 10, there is shown a sheet of material 74 from which a plurality of the second plates 14 are formed. Each of the plates 12, 14, 50, 60, and 68 is preferably formed simultaneously with a plurality of other ones of the plates 12, 14, 50, 60, 68, respectively, by isotropic photo-etching of the entire sheet of material 74 at once. Of course, if other methods are used to form the plates 14, such as cutting with a laser, the plates 14 may also be formed sequentially. Each of the second plates 14 are separated from the rest of the sheet of material 74 by a peripherally extending slot 76, except for two small strips of material 78 attaching opposite ends of each of the second plates 14 to the remainder of the sheet of material 74. A plurality of locating holes 82 are also formed in the sheet of material 74. If desired, identifying indicia, such as part numbers, batch number, etc., can be etched (or otherwise formed) into the sheet of material 74 at a convenient location such as the area 84.

The entire sheet of material 74 can be processed as described above with respect to the single second plate 14, including simultaneously forming a bond pad 20 on each of the second plates 14. Similarly, a sheet of material from which a plurality of first plates 12 (not shown) could have some braze material 40 simultaneously deposited at a respective desired location on each of the first plates 12. Then, as part of the step 104 described above, the sheet of material with the first plates 12 formed therein can be placed onto locating studs 86 of an alignment jig 88, which studs 86 extend through the locating holes (similar to the locating holes 82) formed in the sheet of material to precisely align the sheet of material with respect to the alignment jig 88. In this manner, each of the first plates 12 thereon will be precisely aligned with respect to the alignment jig 88. Next, the sheet of material 74 with the second plates 14 formed therein can be placed onto the same locating studs 86, which studs 86 extend through the locating holes 82 formed in the sheet of material 74 to precisely align the sheet of material 74 with respect to the alignment jig 88. In this manner, each of the second plates 14 thereon will be precisely aligned with respect to the alignment jig 88, and with a respective one of the first plates 12. If braze material is not deposited on the sheet of material containing the first plates 12, braze material in the form of a foil sheet (or a preform) having suitable locating holes formed therethrough could be can be placed onto the same locating studs 86, which studs 86 extend through the locating holes to precisely align the braze material the alignment jig 88, the first plates 12, and the second plates 14 of the sheet of material 74 subsequently placed on the locating studs 86.

When all the lamination layers of the manifold to be constructed are placed on the locating studs 86, the stack of sheets of material can be clamped together and heated then cooled according to the step 105 to braze the lamination layers together forming a plurality of the manifolds 10. The sheet of material 74 and other sheets of material brazed thereto are preferably sized to allow handling by existing automated machinery (such as pick-and-place machines) used in the fabrication of integrated circuits. Preferably, after the sheets of material are brazed together, in the step 106, the components (e.g., the microvalve 19) to be attached to each of the manifolds 10 can be soldered to the respective bond pad 20 of each of the manifolds 10 using automated machinery.

In a step 107, each of the completed manifolds 10 is detached from the sheet of material 74, and the other sheets of materials forming the other laminations of the manifold, by breaking the strips of material 78 (and similar strips of material in the other sheets of material. This is preferably done by automated machinery such as a pick an place machine, which, in the step 108, places the detached manifold 10 in position to be attached to a fluid circuit.

It is anticipated that each of the manifolds 10 thus formed can be tested for leakage or blockage by automated machinery at a suitable point in the manufacturing process, such as after the steps 105, 106, 107, or 108.

In summary, this application presents a novel way of connecting very small openings in a microvalve to a larger pump motor block, in a very small package. Passageways may be routed in different layers so as to cross over each other. Photo-etching allows significant process advantages over stampings—can etch halfway through, no machining stresses or burrs, complete sheets of multiple valve parts can be processed and brazed together allowing pick and place soldering of valves onto the sheet of brazed manifold assemblies. Various brazing options are discussed.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method for forming a manifold, comprising the steps of:
   a) etching a first sheet of material to form a first plate;
   b) etching a second sheet of material to form a second plate;
      b1) forming a bond pad on said outer surface of said second plate;
      b2) disposing a braze material between said first plate and said second plate, wherein said bond pad has a first melting temperature, and said braze material has a second melting temperature less than said first melting temperature;
   c) fixing said first plate to said second plate; and
      c1) heating said first plate, said second plate, said bond pad, and said braze material to a temperature greater than said second melting temperature and less than said first melting temperature until said braze material melts, then cooling said first plate, said second plate, said bond pad, and said braze material to braze said first plate to said second plate.

2. A method for forming a manifold, comprising the steps of:
   a) providing a first sheet of material;
   b) providing a second sheet of material;
   c) forming a first plate and a second plate from said first and second sheets of material by at least one of etching, stamping, machining, cutting, drilling, and milling;
   d) forming a bond pad on an outer surface of said second plate, said bond pad having a first melting temperature;
   e) disposing a braze material having a second melting temperature less than said first melting temperature between said first plate and said second plate;
   f) heating said first plate, said second plate, said bond pad, and said braze material to a temperature greater than said second melting temperature and less than said first melting temperature until said braze material melts; and
   g) cooling said first plate, said second plate, said bond pad, and said braze material until said braze material solidifies to braze said first plate to said second plate.

3. A method for forming a manifold, comprising the steps of:
   a) etching a first sheet of material to form a first plate;
   b) etching a second sheet of material to form a second plate;
   c) forming a bond pad on an outer surface of said second plate said bond pad being formed of a material having a first melting temperature;
   d) disposing a braze material between said first plate and said second plate said braze material having a second melting temperature less than said first melting temperature;
   e) fixing said first plate to said second plate;
   f) heating said first plate, said second plate, said bond pad, and said braze material to a temperature greater than said second melting temperature and less than said first melting temperature until said braze material melts, then cooling said first plate, said second plate, said bond pad, and said braze material to braze said first plate to said second plate; and
   g) fixing a terminal block to the outer surface of said second plate near the bond pad.

4. A method for forming a manifold, comprising the steps of:
   a) etching a first sheet of material to form a first plate having a plurality of first grooves formed therein, said grooves fanning outwardly from closely spaced first bores positioned about a generally circular perimeter having a first diameter;
   b) etching a second sheet of material to form a second plate having a plurality of second grooves formed therein, said grooves fanning inwardly from widely spaced second bores positioned about a generally circular perimeter having a second diameter that is greater than said first diameter;
   c) forming a bond pad on said outer surface of said second plate; and
   d) fixing said first plate to said second plate such that at least one of said first grooves cooperates with a corresponding one of said second grooves to form a fluid passage from an associated one of said first bores to an associated one of said second bores.

* * * * *